United States Patent [19]

Elliott

[11] Patent Number: 4,470,410
[45] Date of Patent: Sep. 11, 1984

[54] PROTECTIVE RETAINING DEVICE AND METHOD

[75] Inventor: Edna M. Elliott, Philadelphia, Pa.

[73] Assignee: Alfred J. Smith, C.M., Philadelphia, Pa.

[21] Appl. No.: 460,135

[22] Filed: Jan. 24, 1983

[51] Int. Cl.³ .............................................. A61M 5/00
[52] U.S. Cl. ............................. 128/133; 128/DIG. 26
[58] Field of Search ................ 128/133, DIG. 26, 132

[56] References Cited

U.S. PATENT DOCUMENTS

| | | | |
|---|---|---|---|
| 2,449,882 | 9/1948 | Daniels | 128/133 |
| 2,727,512 | 12/1955 | Muller | 128/133 |
| 3,167,072 | 1/1965 | Stone et al. | 128/133 |
| 3,722,508 | 3/1973 | Roberts | 128/133 |
| 3,782,378 | 1/1974 | Page | 128/133 |
| 4,059,105 | 11/1977 | Cutruzzula et al. | 128/133 |

*Primary Examiner*—John D. Yasko
*Attorney, Agent, or Firm*—Jacob Trachtman

[57] ABSTRACT

A protective retaining device for application to the site of an intravenous or catheter intervention system utilizing insertion means and tubing comprising an elongated sleeve means of flexible material for being received over and about a portion of the body to which an intervention system is applied. The sleeve means is positionable over the intervention site for protecting the body about and at the site of intervention and for firmly retaining the tubing in position proximate to the body. The retaining device is provided with an opening therein which is positionable over the intervention site of the body to allow inspection of the insertion means without removal or displacement of the retaining device. The invention includes a method for protecting a site of intervention on a body by application and positioning of a flexible sleeve means about the portion of the body at the intervention site and over the insertion means and tubing thereat for firmly retaining between the sleeve means and body the intervention means and minimizing disturbance of the site and dislodgement of the insertion means and tubing secured therewith.

19 Claims, 5 Drawing Figures

U.S. Patent   Sep. 11, 1984   4,470,410
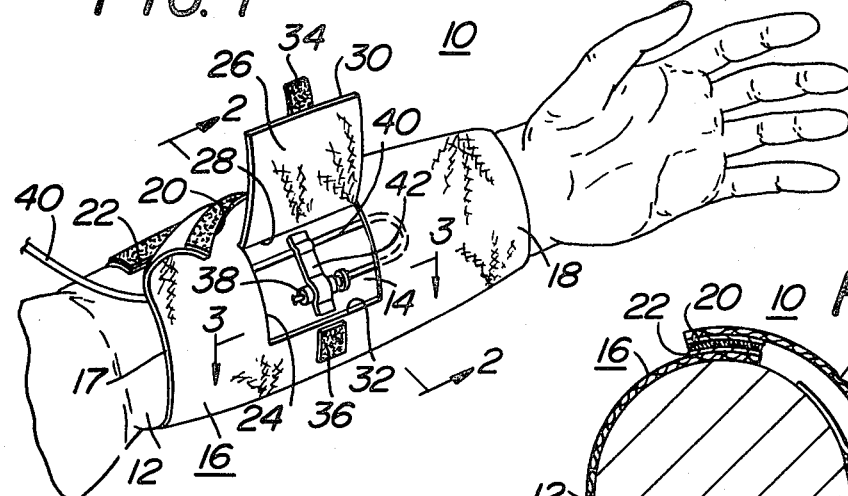
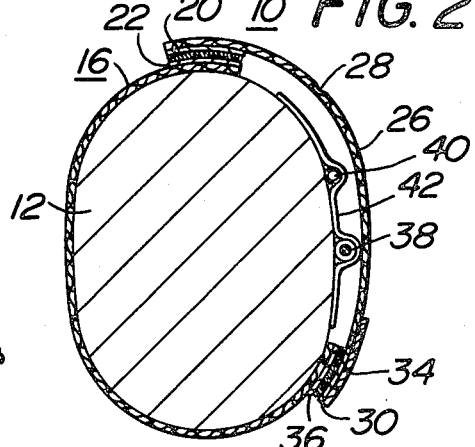
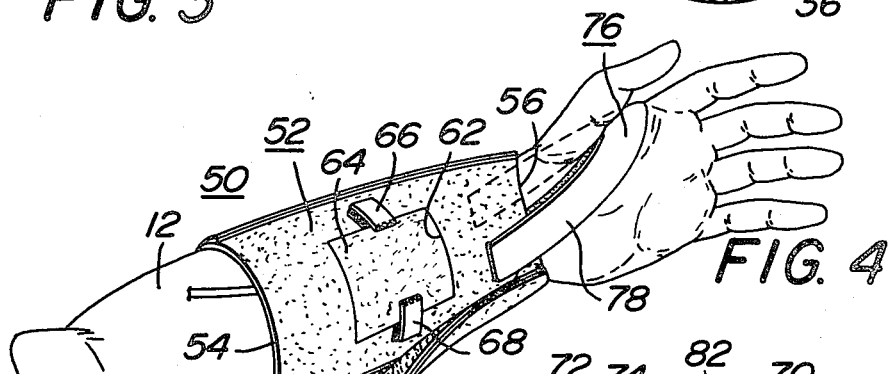
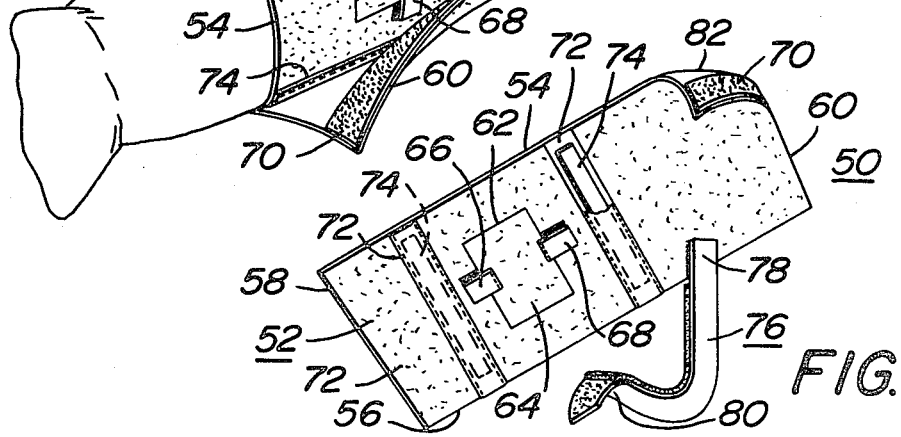

PROTECTIVE RETAINING DEVICE AND METHOD

The invention relates to a device and method for protecting the application site of an intravenous or catheter intervention system, and more particularly to a protective retaining device which is received over and about a portion of a body to which an intervention system is applied for protecting the intervention site and retaining the intervention means in position proximate to the body and the method of applying and utilizing same.

BACKGROUND OF THE INVENTION

Intervention systems have found wide application during medical treatment for intravenous infusion of fluids, drainage of fluids from the body, administering anesthesia, and for surgical testing and other such procedures. Such devices are generally applied at a desired site by puncturing the skin and entering the desired cavity, such as a vein for purposes of infusion, or other regions as may be required. Insertion means, as for example, intravenous needles are utilized to puncture the skin at the site of intervention and appropriate tubing is connected thereto for supplying the desired material to be infused, providing for drainage from the body, or allowing insertion of various catheter means as required. Once such insertion is achieved, it is desirable to limit the movement of the insertion means or needle to avoid accidental removal or inflammation and aggravation of the intervention site. This is important because the repeated insertion of such intervention means, subjects the patient to undesirable emotional distress, increases the difficulty in finding new desirable sites, hinders the application of the desired infusion or drainage of material or other functions being conducted, and takes up much valuable additional time of the hospital personnel attending the patient.

The prior art securing means available for intravenous and catheter retention are not adequate for protecting the site of intervention and preventing dislodgement and accidental removal of the intervention system. Especially in the case of patients who are delirious and not in control of their movements or who may purposefully move their body about in an excessive manner, the site of intervention is disturbed causing dislodgement or the complete removal of the applied means and aggravated inflammation of the body site. The presently available retaining means for intravenous and catheter intervention, are also unsuitable because they do not retain the intervention means with sufficient security to allow the cautious patient the degree of freedom desired for movement without fear of dislodgement. In many instances such devices comprise a plurality of components which are adhered directly to the skin of the patient and not only are difficult to apply and painful to remove, but they are so unsightly that they produce mental distress in sensitive patients, rather than provide an aesthetically desirable appearance.

In certain situations, the limbs of patients have been secured with a rigid surface such as a board, in order to minimize movement and avoid disturbance of the intervention system. In addition to immobilizing the patient and increasing his discomfort, such application can reduce the circulation of the patient and impede the flow of the transmitted fluids thereby reducing the recovery rate. Such application is also undesirable because of the increased time and effort required for administration of the intervention. The methods now used for applying the prior art retention means to a patient are also cumbersome, time consuming and require a team of personnel to accomplish the desired application.

SUMMARY OF THE INVENTION

It is therefore a primary object of the invention is to provide a new and improved protective retaining device which protects the intervention site and firmly retains the intervention means against dislodgement and removal and a method of readily applying and positioning same at the intervention site of a body.

Another object of the invention is to provide a new and improved protective retaining device and means for applying same to a body which provides protective padding for the intervention site, and minimizes movement and dislodgement of the insertion means at the intervention site without reducing circulation of the patient or the flow rate of fluids being infused or drained.

Another object of the invention is to provide a new and improved protective retaining device and method of applying same to a body which may be quickly and efficiently applied especially in emergency situations and which minimizes the risk of excessive blood loss or infection due to cannular tubing dislodgement.

Another object of the invention is to provide a new and improved protective retaining device and method of applying same which minimizes the risk of infiltration and motion phlebits and the requirement for reinserting of the insertion means by repeated puncture of the patient's skin.

Another object of the invention is to provide a new and improve protective retaining device which may readily be applied to and about the various limbs of the body, is adaptable for application to the skull cap as where the intervention means is applied to the skull veins of neonates, and is adaptable for application to protect the umbilical lines.

Another object of the invention is to provide a new and improved protective retaining device for intervention means and method of applying same which readily allows inspection of the insertion site without removal or displacement of the retaining device.

Another object of the invention is to provide a new and improved protective retaining device which is garment like and more visually acceptable to patients by avoiding the appearance of tubing emanating directly from the patient's body.

Another object of the invention is to provide a new and improved protective retaining means and a method of applying same which does not require the use of an arm board for disoriented patients or those subject to rapid and uncontrolled movements.

Another object of the invention is to provide a new and improved protective retaining device which is especially acceptable to pediatric patients who are frequently frightened by tubing and tape and which allows a patient to view the device as a more normal accessory for his person.

Another object of the invention is to provide a new and improved protective retaining device which provides the desired security to permit the wearer to more normally use the arm or limb of the body to which the intervention means is applied without fear of displacement or dislodgement of same and the requirement for reinsertion.

Another object of the invention is to provide a new and improved protective retaining device and method which stabilizes the site of intervention and removes the fear of the intervention procedures and applications.

Another object of the invention is to provide a new and improved protective retaining device and method of applying same which is adaptable for chemotherapy by allowing the patient to travel with a heparin lock in the vein while being assured of the security provided by the protective retaining device.

Another object of the invention is provide a new and improved protective retaining device and method of applying same which is simple in construction, low in cost and which may readily be applied and used by inexperienced personnel.

The above objects as well as many other advantages of the invention are achieved by providing a protective retaining device for application to the site of an intravenous or catheter intervention system utilizing insertion means and tubing comprising an elongated sleeve means of flexible material for being received over and about a portion of the body to which the intervention system is applied. The sleeve is positionable over the intervention site for protecting the body about and at the site of intervention and for retaining the tubing in position proximate to the body. The retaining device is provided with an opening therein which is positionable over the intervention site of the body to allow inspection of the insertion means without removal or displacement of the retaining device. The sleeve means is provided with a flap which covers the opening and the site of application of the intervention system, which flap is movable to uncover the opening and expose for inspection the site and the application of the insertion means to the body.

The sleeve means of the protective retaining device may be in a form having a flat substantially rectangular configuration before application with first and second opposite longitudinal side edges and first and second opposite end edges. Attachment means are provided proximate to and along at least one of the side edges for detachably securing same with the sleeve means to maintain the sleeve means in position after it is wrapped about the body and over the insertion means and attached tubing at the site of intervention. The sleeve means is also provided with a cover enclosing the opening of the sleeve means and protecting the site of the insertion means. The cover is detachable to uncover the opening and expose for inspection the site of application of the insertion means to the body and may be replaced by a fresh cover as required. The sleeve means is desirably provided with a smooth and moisture absorbing inner surface for contacting the portion of the body about which it is to be secured, and the detachable securing means can be provided by micro hook means for allowing adjustable attachment. In one form, the sleeve means is of an elastic material which is stretchable for being received over the body at the site of intervention and positioned to have a tubular form about the body with its opening over the site of intervention. The sleeve means contracts in position for firmly retaining the tubing connected with the insertion means and minimizing disturbances of the intervention site and dislodgement of the insertion means. In another form, the sleeve means is of a substantially non stretchable material which is wrapped about the body and secured at its side edges to provide the desired tension and may have a thickness sufficient to provide a desired protective padding. The method of applying such form of the protective retaining device is by holding to the body one of the side edges of the sleeve and wrapping the sleeve means about the portion of the body so that the sleeve means overlies and retains the insertion means and tubing therewithin, and then securing the detachable means of the second side edge with the sleeve means to apply the desired tension for retaining the sleeve means in position on the portion of the body about which it is wrapped.

The foregoing and other objects of the invention will become more apparent as the following detailed description is read in conjunction with the drawing, in which:

DESCRIPTION OF THE DRAWING

FIG. 1 is a perspective view of a protective retaining device of the invention as applied about an intervention site on the arm of a patient, FIG. 2 is a sectional view taken on line 2—2 of FIG. 1 with the cover in its closed position, FIG. 3 is a sectional view taken on line 3—3 of FIG. 1 with the cover in its closed position, FIG. 4 is a perspective view similar to that of FIG. 1 illustrating a modified form of the protective retaining device, and FIG. 5 is a plane view of the protective retaining device of FIG. 4 prior to its application.

Like reference numerals designate like parts throughout the several views.

DETAILED DESCRIPTION

FIGS. 1 to 3 illustrate a protective retaining device 10 of the invention applied to the lower left arm 12 of a patient having an intervention site 14. The protective retaining device 10 comprises a sleeve means 16 which may be of an elastic stretchable material. Before application, the sleeve means 16 when positioned flat has a substantially rectangular configuration with opposite end edges 17 and 18, and opposite longitudinal side edges 20 and 22. The sleeve means 16 is provided with a rectangular opening 24 intermediate its end edges 17, 18, and end edges 20, 22. The opening 24 is formed by being cut out to provide a flap 26 which is hinged along one edge 28 at the opening 24 as illustrated in FIG. 1. The other opposite edge 30 of the flap 26 is received proximate to the edge 32 of the opening 24 when the flap 26 is positioned to cover the site 14 of intervention. A retaining tab 34 is secured with the top of the flap 26 and can be detachably secured with a securing patch 36 which is positioned on the sleeve means 16 proximate to the edge 32 of the opening for retaining the flap 26 in its closed position. The tab and patch 34 and 36 may be provided with micro hook attaching means for being detachably secured. The longitudinal side edges 20 and 22 of the protective retaining device 10 are also provided with detachable attachment means therealong which similarly may be of the micro hook type for securing the edges together, or if the edges are overlapped securing same with the adjacent surface of the sleeve means 16 after the retaining means 10 has been applied about the arm 12.

The protective retaining device 10 is applied to protect the intervention site 14 after the intervention system has been applied to the arm 12 of the patient. As illustrated in FIG. 1, the intervention system may comprise an insertion means 38, such as a needle for piercing the skin at the intervention site 14 and being inserted into a vein. The insertion means 38 is joined with connecting tubing 40 and is usually initially located and retained in place by a short strip of adhesive tape 42. The protective retaining device 10 is applied by first positioning its side edge 22 to extend in the direction between the elbow and wrist of the patient and displaced from the intervention site 14. With the side edge 22 held in this position, the remaining portion of the device 10 is wrapped around the arm, so that the opening 24 is positioned over the intervention site 14, and the edge 20 with its retention means is engaged along the complimentary retention means of the edge 22. The application of the retaining device 10 stretches the resilient material of the sleeve meas 16 so that it applies a desired tension securely maintaining same in position about the body and firmly retaining the tubing 40 proximate to the body and minimizing disturbance of the intervention site and dislodgement of the insertion means and tubing of the intervention system.

The intervention site 14 is covered and protected by the flap 26 in its closed position, while the site 14 may readily be inspected by detaching the tab 34 and moving the flap 26 to its open position without disturbing the protective sleeve means 16 or interferring with its retention of the intervention system.

When the protective device 10 is worn by the patient, the intervention site 14 is completely enclosed and non-visible and only the extending portion 42 of the tubing emerges, thereby providing the patient with a more acceptable and less frightening appearance, which is especially desirable for those who are sensitive to viewing medical appliances. The application of the protective retaining device 10, also provides the patient with a high degree of freedom of movement without fear of dislodging the insertion means or injuring his body. The protective retaining means 10, is readily applied and removed when required as noted above causing minimal discomfort to the patient. Where a patient is receiving chemotherapy and utilizes a heparin lock at the intervention site, the patient can be ambulatory and travel while being assured of the security provided by the protective retaining device.

The sleeve means 16 may be made of material which is moisture absorbent and permits air circulation, and in sizes desirable for different portions of the anatomy about which it is to be received. The tension and firmness with which the protective device is secured about the body may readily be adjusted by the size of the device utilized and the degree to which the elastic material is stretched. The side edges 20 and 22 may be overlapped to increase the retaining force without unduly restricting the operation of the intervention system and the comfort of the patient.

The FIGS. 4 and 5 disclose a protective retaining device 50 of the invention, which is a modified form of the device 10 of FIG. 1. Because of its many similarities with the device 10, only the differences of the device 50 will be discussed in detail. The device 50 comprises a sleeve means 52 made of a substantially non stretchable material which is applied to the site of intervention by wrapped about the body 12 or region of application as described in connection with the device 10. The sleeve means 52 is provided with a thickness sufficient to provide a padding for protecting the portion of the body over which it is received. The sleeve means 52, as shown in FIG. 5, has a substantially rectangular configuration when it is in its flat form before application. The sleeve means 52 has end edges 54 and 56, and longitudinal side edges 58 and 60. The sleeve 52 has a rectangular opening 62 which is enclosed by a rectangular cover 64. The cover 64 is completely removable, so that it may be replaced with a fresh cover 64 if it is soiled with blood or other fluid materials as may occur during the intervention process. The cover 64 has a pair of attaching tabs 66, 68 at opposite sides which may include micro hook attachment means for being retained over the opening 62. The underside of the device 50 proximate to the side edge 60 may be provided with a strip 70 of micro hook material for being secured with the top surface of the sleeve 52 at the region 72 for positioning and tensioning same about the arm 12 or body portion of the patient. For providing additional stability and preventing distortion of the opening 62, a pair of narrow pockets 72 are provided on each side of the opening 62 extending in the direction between the end edges 54 and 56. An elongated stay element 74, is received within each of the pockets 72 for equalizing tension applied by the retaining device 50 over the intervention site. The inner surface 82 of the sleeve means 52 which contacts the skin of the patient is desirably smooth to avoid irritation and moisture absorbent.

The protective retaining device 50 is applied in a manner similar that in which the device 10 is applied over and about the intervention site. In this case, since the material is non elastic, control of tension is obtained by the manner in which the device is wrapped about the body and the force which is applied when the side end 60 is secured with the surface at the region 72. An elongated retaining band 76 with a bottom surface of micro hook retaining material provides additional stability for positioning the sleeve means 52 on the body, and preventing its shifting or riding up on the arm or limb of the patient. After one end 78 of the band 76 is secured with the sleeve means 52, the band is positioned between the thumb and forefinger of the hand as illustrated in FIG. 3 and the other end 80 is adjustably secured with the sleeve means to achieve the additional security.

Although only two particular embodiments of the invention have been described in detail, it is noted that the protective retaining device of the invention may have various forms while still providing the advantages of the invention. Thus, for example, the device 10 which provides a sleeve meanas 16 of stretchable material having a rectangular configuration, may alternately be formed to provide a unitary tubular sleeve element which is stretchable for being positioned over the body at the intervention site with its opening positioned to expose the intervention site for providing the required inspections. The sleeve means of the protective retaining device may also be dimensioned and adapted for being received about the skull of a patient, as in the case where intervention is provided to the skull veins of neonates, as well as having other desired particular forms which will be obvious to those versed in the art.

It will, thus, of course, be understood that the description and the drawings herein contained, are illustrative, merely, and that various modification and changes may be made in the structures and method disclosed without departing from the spirit of the invention.

What is claimed is:

1. A protective retaining device for application to the site of an intravenous or catheter intervention system utilizing insertion means and tubing comprising a unitary continuous sleeve means of flexible material providing an elongated tubular form for completely encompassing a body and being received over and about a portion of the body to which an intervention system is applied, the sleeve means being positionable over the intervention site for protecting the body about and at the site of intervention and for firmly retaining the tubing in position proximate to the body, the retaining device being provided with an opening therein which is positionable over the intervention site of the body to allow inspection of the insertion means without removal or displacement of the retaining device.

2. The protective retaining device of claim 1 in which the sleeve means is of elastic material.

3. The protective retaining device of claim 1 in which the sleeve means is provided with a displaceable cover over the opening of the sleeve and the site of applcation of the intervention system which is movable for uncovering the opening and exposing for inspection the site of application to the body of the insertion system.

4. The protective retaining device of claim 1 in which the sleeve means has a substantially rectangular configuration with first and second opposite longitudinal side edges, the sleeve means includes attachment means proximate to and along at least one of the side edges for detachably securing the side edge with the sleeve means for maintaining the sleeve means in position after it is wrapped about the body and over the insertion means and tubing at the site of the intervention.

5. The protective retaining device of claim 4 in which the sleeve means is of a moisture absorbent material.

6. The protective retaining device of claim 4 in which the sleeve means is provided with a displaceable cover enclosing the opening of the sleeve means and covering the site of application of the insertion means which cover is movable without removal or displacement of the sleeve means to uncover the opening and expose for inspection the site of application to the body of the insertion means.

7. A protective retaining device for application to the site of an intravenous or catheter intervention system utilizing insertion means and tubing comprising an elongated sleeve means of flexible material providing an elongated tubular form for being received over and about a portion of a body to which an intervention system is applied, the sleeve means being positionable over the intervention site for protecting the body about and at the site of intervention and for firmly retaining the tubing in position proximate to the body, the sleeve means being provided with an opening therein which is positionable over the intervention site of the body to allow inspection of the insertion means without removal or displacement of the retaining device, the sleeve means being provided with a cover over the opening of the sleeve means which is movable for uncovering the opening and exposing for inspection the site of application to the body of the insertion system, the opening of the sleeve means being provided by a cut out portion having opposite sides, and the cover being a flap of the flexible material of the sleeve means which is secured at one side of the cut out portion and extends over the opening and is detachably secured at the other side of the cut out portion for enclosing the opening.

8. The protective retaining device of claim 7 in which the sleeve means is of an elastic and moisture absorbent material.

9. A protective retaining device for application to the side of an intravenous or catheter intervention system utilizing insertion means and tubing comprising an elongated sleeve means of flexible material for being received over and about a portion of a body to which an intervention system is applied, the sleeve means being positionable over the intervention site for protecting the body about and at the site of intervention and for firmly retaining the tubing in position proximate to the body, the sleeve means having a substantially rectangular configuration with first and second opposite longitudinal side edges and including attachment means proximate to and along at least one of the side edges for detachably securing the side edge with the sleeve means for maintaining the sleeve means in position after it is wrapped about the body and over the insertion means and tubing at the site of the intervention, the sleeve means being provided with an opening therein provided by a cut out portion with opposite sides which is positionable over the intervention site of the body to allow inspection of the insertion means without removal or displacement of the retaining device and a detachable cover enclosing the opening of the sleeve means and covering the site of application of the insertion means which cover is detachable to uncover the opening and expose for inspection the site of application to the body of the insertion means and the cover being secured at the opposite sides of the cut out portion by detachable means and extends over to enclose the opening and being removable for exposing the site of the body at the opening and for being replaced.

10. The protective retaining device of claim 9 in which the sleeve means has a smooth moisture absorbing surface for contacting the portion of the body about which it is to be received, and the detachable securing means are provided by micro hook attachment means.

11. The protective retaining device of claim 10 which includes an elongated retaining band having ends adjustably secured with the sleeve means which is receivable about an extremity of the body proximate to the sleeve means for resisting displacement on the body of the sleeve means.

12. The protective retaining device for application to the site of an intravenous or catheter intervention system utilizing insertion means and tubing comprising an elongated sleeve means of flexible material for being received over and about a portion of a body to which an intervention system is applied, the sleeve means being positionable over the intervention site for protecting the body about and at the site of intervention and for firmly retaining the tubing in position proximate to the body, the sleeve means having a substantially rectangular configuration with first and second opposite longitudinal side edges and including attachment means proximate to and along at least one of the side edges for detachably securing the side edge with the sleeve means for maintaining the sleeve means in position after it is wrapped about the body and over the insertion means and tubing at the site of the intervention, the sleeve means being provided with an opening therein which is positionable over the intervention site of the body to allow inspection of the insertion means without removal or displacement of the retaining device and a cover enclosing the opening of the sleeve means and covering the site of application of the insertion means which cover is detachable to uncover the opening and expose for inspection the site of application to the body of the insertion means, the sleeve member including a pair of longitudinally extending flexible stay elements on opposite sides of the opening for stabilizing and equalizing the force applied to the body by the sleeve about the site of the invention.

13. A method for protecting and allowing the inspection of a site of intervention and an intravenous or catheter intervention system applied to a body by implanting insertion means in a portion of a body at a selected site and tubing connected therewith, comprising the steps of applying about a body including the portion of the body having the intervention site and over the insertion means and tubing thereat an elongated flexible sleeve means firmly retaining the tubing between the sleeve means and body for minimizing disturbance of the intervention site and dislodgement of the insertion means and tubing of the intervention system, positioning the opening of the sleeve means to overlie the intervention site to allow its inspection without removal or displacement of the sleeve means about the body, and positioning an elongated retaining band about an extremity of the body proximate to the sleeve means, securing one end of the band with the sleeve means, and adjustably securing the other end of the band with the sleeve means for tensioning the band to resist displacement of the sleeve means on the body.

14. The method of claim 13 in which the flexible sleeve means is of an elastic material and is stretched for being applied over the site of intervention and after being positioned is released to apply compressive force to the tubing positioned between it and the body for firmly retaining the intervention system and minimizing disturbance of the intervention site and dislodgement of the insertion means and tubing secured therewith.

15. The method of claim 14 in which the opening of the sleeve means has a cover and includes the step of displacing the cover without removal or displacement of the sleeve means for allowing inspection of the intervention site and replacing the cover for protecting the body and the intervention system at the intervention site.

16. The method of claim 13 in which the flexible sleeve means is substantially rectangular having first and second opposite longitudinal side edges with at least the second of the side edges being provided with means for being detachably secured with the sleeve means, and in the step of applying the sleeve means to the body, placing the first of the side edges on the body and wrapping the sleeve means about the body including the portion of the body having the intervention site so that the sleeve means overlies the insertion means and retains therewithin the tubing thereat and the second edge overlaps the sleeve means, and securing the detachable means of the second edge with the sleeve means so as to apply a desired tension for retaining the sleeve means in position on the portion of the body about which it is wrapped.

17. The method of claim 16 in which the opening of the sleeve means has a cover, and includes the step of displacing the cover for allowing inspection of the intervention site and replacing the cover over the opening for protecting the intervention means and the body at the intervention site.

18. The method of claim 13 in which the opening of the sleeve means has a cover and includes the step of displacing the cover without removal or displacement of the sleeve means for allowing inspection of the intervention site and replacing the cover for protecting the body and the intervention system at the intervention site.

19. The method of claim 13 in which the opening of the sleeve means has a cover, and includes the step of removing the cover for allowing inspection of the intervention site and replacing the cover over the opening for protecting the intervention means and the body at the intervention site.

* * * * *